(12) United States Patent
Altman

(10) Patent No.: US 6,716,242 B1
(45) Date of Patent: Apr. 6, 2004

(54) PULMONARY VEIN STENT AND METHOD FOR USE

(76) Inventor: Peter A. Altman, 384 Oyster Point Blvd. #4, South San Francisco, CA (US) 94080

( * ) Notice: Subject to any disclaimer, the term of this patent is extended or adjusted under 35 U.S.C. 154(b) by 0 days.

(21) Appl. No.: 09/687,776

(22) Filed: Oct. 13, 2000

Related U.S. Application Data

(60) Provisional application No. 60/159,343, filed on Oct. 13, 1999.

(51) Int. Cl.$^7$ ................................................. A61F 2/06
(52) U.S. Cl. ..................... 623/1.42; 623/1.44; 623/1.46; 623/1.15; 427/2.25
(58) Field of Search ............................. 623/1.42–1.48, 623/11.11, 12, 23.7; 606/191–192, 194–195, 198; 427/2.24–2.25

(56) References Cited

U.S. PATENT DOCUMENTS

| | | | | |
|---|---|---|---|---|
| 5,527,344 A | | 6/1996 | Arzbaecher et al. | 607/3 |
| 5,538,504 A | * | 7/1996 | Linden et al. | 604/264 |
| 5,609,151 A | | 3/1997 | Mulier et al. | 128/642 |
| 5,725,567 A | | 3/1998 | Wolff et al. | 623/1 |
| 5,769,883 A | | 6/1998 | Buscemi et al. | 623/1 |
| 5,891,108 A | | 4/1999 | Leone et al. | 604/264 |
| 5,899,917 A | | 5/1999 | Edwards et al. | 606/195 |
| 6,012,457 A | | 1/2000 | Lesh | 128/898 |
| 6,024,740 A | | 2/2000 | Lesh et al. | 606/34 |
| 6,099,562 A | * | 8/2000 | Ding et al. | 424/424 |
| 6,113,567 A | | 9/2000 | Becker | 604/8 |
| 6,117,101 A | | 9/2000 | Diedrich et al. | 604/22 |
| 6,206,914 B1 | * | 3/2001 | Soykan et al. | 604/891.1 |
| 6,511,477 B2 | * | 1/2003 | Altman et al. | 606/41 |
| 2001/0046518 A1 | * | 11/2001 | Sawhney | |
| 2002/0082680 A1 | * | 6/2002 | Shanley et al. | 623/1.16 |

FOREIGN PATENT DOCUMENTS

| | | |
|---|---|---|
| WO | WO 99/52423 | 10/1999 |
| WO | WO 00/42934 | 6/2000 |

OTHER PUBLICATIONS de Levie, Robert: The Admittance of the Interface between a Metal Electrode and an Aqueous Electrolyte Solution: Some Problems and Pitfalls, pp. 337–347, Annals of Biomedical Engineering, Special Issue.

Scheinman, Melvin: Supraventricular Tachycardia: Drug Therapy Versus Catheter Ablation, Clinical Cardiology, vol. 17, Supp. II–11–II–15 (1994).

\* cited by examiner

*Primary Examiner*—David J. Isabella
*Assistant Examiner*—Urmi Chattopadhyay

(57) ABSTRACT

Ablation of the pulmonary veins causes damage to the tissue which may affect the viability of the tissue. By placing a stent, a vascular endoprosthesis, within a target pulmonary vein it is possible to protect the functionality of the veins after the ablation procedure. Placement of a stent, endoprosthesis or mere circuit interrupting structure into a target pulmonary vein, without ablation, prevents aberrant electrical activity in the pulmonary veins from interfering with the electrical activity of the left atrium. The stent, endoprosthesis or circuit interrupting structure may also be coated or comprised of a drug-eluting compound, loaded with a drug which inhibits arrhythmia.

6 Claims, 4 Drawing Sheets

PULMONARY VEIN STENT AND METHOD FOR USE

RELATED PATENT APPLICATION

This patent application claims priority to provisional patent application No. 60/159,343, filed Oct. 13, 1999.

FIELD OF THE INVENTIONS

The inventions described below relate to the field of implantable medical devices. Specifically the invention relates to endoluminally placed prosthesis known as stents. More specifically, the invention relates to the placement of stents in the pulmonary veins which have advantages for the treatment of atrial fibrillation.

BACKGROUND OF THE INVENTIONS

Atrial fibrillation (AF) is a form of heart disease that afflicts millions of people. It is a condition in which the normal contraction of the heart is interrupted, primarily by abnormal and uncontrolled action of the atria of the heart. The heart has four chambers: the right atrium, right ventricle, the left ventricle, and the left atrium. The right atrium pumps de-oxygenated blood from the vena cava to the right ventricle, which pumps the blood to the lungs, necessary for return flow of de-oxygenated blood from the body. The right atrium contracts to squeeze blood into the right ventricle, and expands to suck blood from the vena cava. The left atrium pumps oxygenated blood from the pulmonary veins (returning from the lungs), necessary for flow of oxygenated blood from the lungs. The left atrium contracts to squeeze blood into the left ventricle, which then pumps the blood into the aorta and thence to the entire body, and expands to suck blood from the pulmonary veins. The contractions of the atria normally occur in a controlled sequence with the contractions of the other chambers of the heart. When the left atrium or the right atrium fails to contract, contracts out of sequence, or contracts ineffectively, blood flow within the heart is disrupted. The disruption of the normal rhythm of contraction is referred to as an arrhythmia. The arrhythmia, known as atrial fibrillation, can cause weakness of the heart due to reduced ventricular filling and reduced cardiac output, stroke due to clot formation in a poorly contracting atria, which may lead to brain damage and death, and even life threatening ventricular arrhythmias.

There is a broad spectrum of situations which fall under the broad heading of AF. For example, in older patients where there is substantial heterogeneity in the conduction within the atrial tissue, the patient is said to have the tissue substrate for AF such that any trigger will result in maintaining AF. In younger patients, the tissue may have more homogeneous conduction and be less likely to have sustained AF. In the younger patient it may be the often reoccurrence of a premature depolarizing tissue which acts as a trigger that causes the clinical manifestation of problematic episodes of AF. Clearly, there is a continuous spectrum of degrees of triggered AF and conduction heterogeneity which acts as a substrate for this arrhythmia, and it is appropriate that a number of medical therapies are being developed to treat this disease.

Atrial fibrillation may be treated with an atrial defibrillator. Atrial defibrillators are typically implantable electrical therapy devices which deliver defibrillating energy to the atrium to terminate arrhythmias. They sense the electrical activity of the atrium and deliver an electrical shock to the atrium when the electrical activity indicates that the atrium is in fibrillation. Electrical defibrillation has two major problems: the therapy causes substantial pain, and has the potential to initiate a life threatening ventricular arrhythmias. The pain associated with the electrical shock is severe and unacceptable for many patients. Unlike electrical ventricular defibrillators, where the patient loses consciousness prior to receiving therapy, the patient who suffers an atrial arrhythmia is conscious and alert when the device delivers electrical therapy.

The potential for inappropriate induction of ventricular fibrillation by the shock intended to defibrillate the atrium exists. The induction of ventricular fibrillation has great potential to result in death in just a few minutes if no intervening therapy is provided. Even with careful algorithms to deliver shocks to the periods in the ventricular contraction cycle when the heart is not susceptible to shock induced ventricular fibrillation, the risk of setting off a ventricular fibrillation remains substantial.

Doctors have treated atrial fibrillation with drugs injected intravenously or administered orally. Recent literature describes the potential for the delivery of drugs to the heart on demand to terminate arrhythmias. The concept has been suggested for use in the atrium to treat atrial fibrillation. Arzbaecher, Pharmacologic Atrial Defibrillator and Method, U.S. Pat. No. 5,527,344 (Jun. 18, 1996) describes a pharmacological atrial defibrillator and method for automatically delivering a defibrillating drug into the bloodstream of a patient upon detection of atrial arrhythmias in order to terminate the atrial arrhythmias. Arzbaecher teaches that unspecified defibrillating drugs should be injected into the bloodstream with a large initial dose followed by delivery of a continuous smaller dose (this is the "two-compartment pharmacokinetic model" discussed in the Arzbaecher patent). By delivering agents to a blood vessel and maintaining a therapeutic level of drugs in the blood stream, Arzbaecher requires systemic effects to be achieved in order to terminate atrial arrhythmias. In other words, if drugs injected according to Arzbaecher are to have any effective concentrations within the heart, then a large amount must be injected in the blood stream to ensure that an adequate dose is delivered to the affected area of the heart. While the drugs are in the blood stream, they are available throughout the body to cause side effects on all other organs.

There are several disadvantages to the transient introduction of systemic drug levels by an implantable device. Systemic effects resulting from such delivery may result in detrimental effects to ventricular cardiac conduction. These detrimental effects could be life threatening, and several studies suggest that use of these drugs actually leads to higher mortality. The large amount of drugs required for systemic delivery of therapeutic doses demands a larger, less comfortable device than smaller dosages would allow. The large quantity of drug in the implantable reservoir of such a system is potentially more dangerous if it develops a leak or is ruptured. Such a large single dosage requires a reservoir that requires frequent follow-ups for refilling post therapy by a clinician. Lastly, the large quantity of drugs required to obtain therapeutic levels in the entire body may cost substantially more than that required to treat a specific site within the heart.

Atrial fibrillation can be treated by atrial ablation. There are two general approaches for providing ablative therapy to the heart for the treatment of atrial fibrillation. These shall be called the long linear ablative lesion approach and the focal ablation approach.

In the long linear lesion approach, the heart tissue is killed along a linear pathway. The cardiac electrophysiologist does this to segment the heart into regions which are too small to sustain atrial fibrillation. Such an approach is very similar to performing the Maze procedure using radiofrequency, microwave, and ultrasound ablative energy sources on the end of catheters. In the Maze procedure, a number of incisions are made with a scalpel in an attempt to terminate inappropriate accessory pathways.

In the focal ablation approach, the heart tissue is killed at a single site. The cardiac electrophysiologist attempts to ablate the region of the heart that prematurely depolarizes, and which has been described as acting as a trigger for the initiation of atrial fibrillation. Recently, work in ablating regions at the junction of the pulmonary veins and the left atrium has been performed. Such ablations remove the possibility of triggers for AF initiating within the pulmonary veins, or at the region near the junction of the veins with the left atrial tissue. Such ablations may also remove disturbances introduced into the conduction pathway by the heterogeneity of the junction region anatomy.

SUMMARY

Focal ablation of the region within or adjacent to the pulmonary vein to terminate atrial fibrillation with different energy transfer techniques such as cryoablation, RF ablation, laser ablation, ultrasound ablation, and microwave ablation causes damage to the tissue which may affect the viability of the tissue. By placing a stent, a vascular endoprosthesis, within a target pulmonary vein it is possible to protect the functionality of the veins after the ablation procedure.

In some cases, placement of a stent, endoprosthesis or mere circuit interrupting structure into the pulmonary veins prevents aberrant electrical activity in the pulmonary veins from interfering with the electrical activity of the left atrium and thereby eliminate the need for destructive ablation. The stent, endoprosthesis or circuit interrupting structure may be coated or comprised of a drug-eluting compound, loaded with a drug which inhibits arrhythmia. Embodiments include a new indication for maintaining vessel patency after a destructive ablation procedure, and the use of a stent both with and without local drug delivery to disrupt the electrical contribution of the pulmonary veins to atrial electrical activity leading to the induction and maintenance of atrial fibrillation.

DETAILED DESCRIPTION OF THE INVENTIONS

Figure 1:
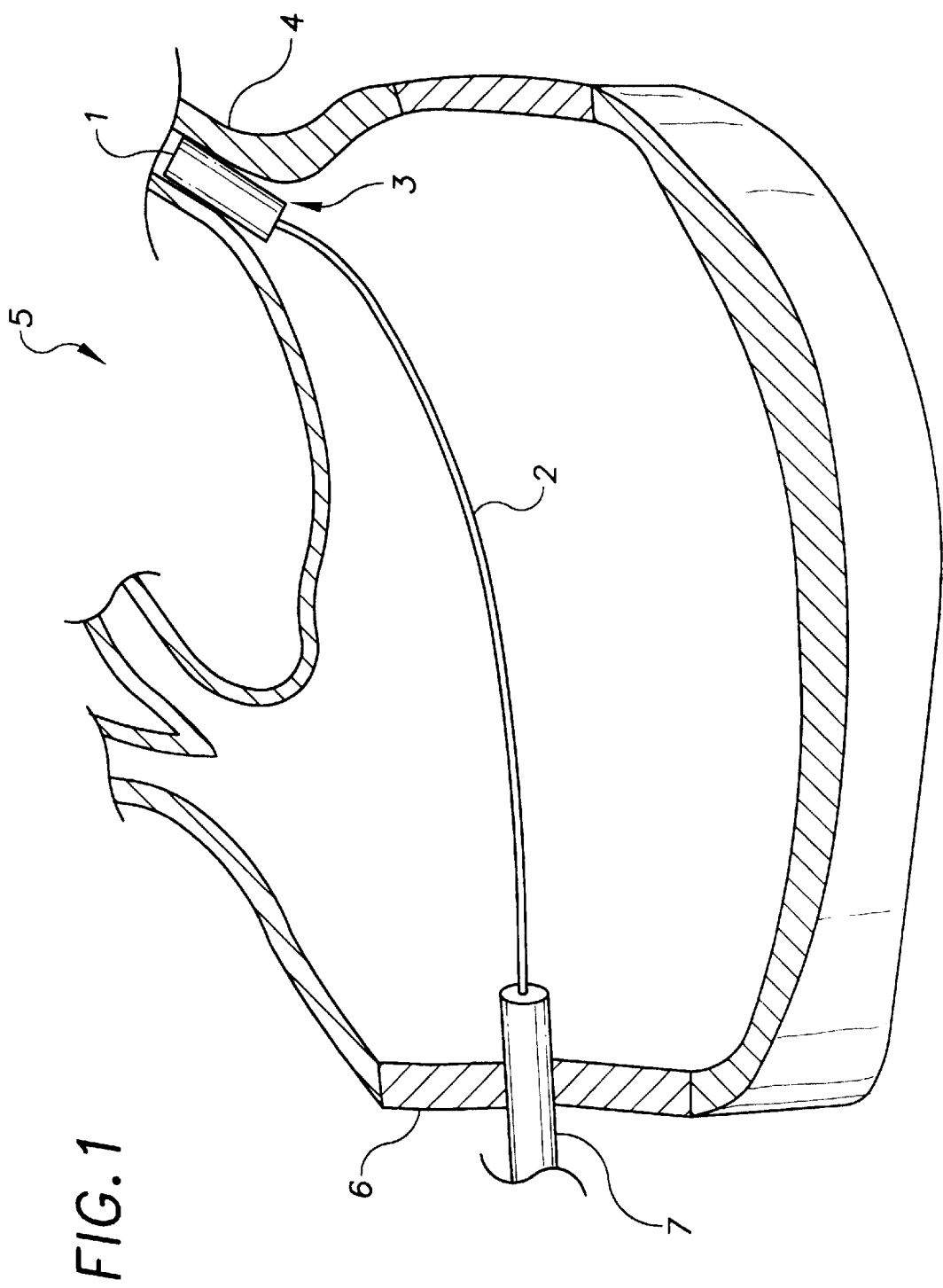
FIG. 1 is a cross-sectional view of the left atrium with the stent deployed into the target pulmonary vein.

In FIG. 1 the stent 1 has been deployed, by the catheter 2, into the ostium 3 of the target pulmonary vein 4. The stent alone acts to isolate the electrical impulses of the pulmonary veins from the atrial conduction tissue. The stent, endoprosthesis or circuit interrupting structure is placed into the ostium of the target pulmonary veins. The term "stent" is being used in its broad sense as is meant to encompass a stent, endoprosthesis or a circuit interrupting structure. The stent, when fabricated of a material with desirable electrical properties (for example, metal, which has a low resistivity) may comprise the circuit interrupting structure. To place the stent in the target pulmonary vein, access to the left atrium 5 is first gained by percutaneous insertion of a catheter into the left atrium. To accomplish this, a needle catheter is placed through the venous system into the right atrium, and then penetrates the fossa ovalis 6 (the atrial septum) to gain access to the left atrium. Access to the right atrium (not shown) can be through the femoral vein in the thigh and the inferior vena cava, or may be through the subclavian vein, brachial vein or cephalic vein, etc., in the shoulder and arm, and then through the superior vena cava. A catheter sheath 7, such as a guiding catheter, is advanced over the needle catheter and is inserted into the left atrium. The needle catheter is then removed, and a stent delivery catheter is inserted with a stent loaded on the distal end of the catheter. The distal end of the catheter is then maneuvered into the left atrium and into the target pulmonary veins. Location of the stent is confirmed and the stent is expanded or released, and expanded to the point where it securely engages the wall of the pulmonary vein. If necessary, the stent may be pressed into the wall of the pulmonary vein, and may have fastening appendages such as barbs, to more securely attach to the pulmonary vein wall.

As previously noted, placement of the stent alone can act to isolate the target pulmonary vein from the atrial conduction and excitation process. The primary advantage of this method is that no tissue is damaged. The ramifications regarding the viability of the pulmonary veins long term is obvious. Less obvious is the fact that the non-damaging procedure can be reversed, if desired. This stent device may operate by acting as an electrically insulative barrier to an electrical signal, a capacitively coupled short across the region of tissue in question, an averager that reduces the effective signal of the myocardial region in question, a substrate for the delivery of pharmacological agents to alter the electrical excitation and conduction properties of the local tissue region, or any combination of these mechanisms. The preferred embodiment incorporates local delivery of therapeutic agents to a region equivalent to the lumen wall on the outer wall of the stent.

Where placement of the stent is accomplished without an accompanying ablation procedure, the device may be fabricated in various forms. A nonconductive embodiment of any of the different possible geometries of the device will act as an insulative barrier preventing conduction through the device, and acting similarly to a region of necrotic tissue created by ablation. There is one fundamental difference: the device disclosed here changes the cellular conductivity locally without destroying tissue.

The conductive embodiments of the device act as a short across the pulmonary vein region which may introduce a triggered premature depolarization of cells. By electrically connecting the tissue around the arrhythmogenic site, the cells on either side of a conductive device will be coupled capacitively to the device and therefore to each other.

Metals are very efficient conductors of electrons, but not for ions. On the other hand, aqueous electrolyte solutions are ionic conductors and are hostile to electrons. Consequently, at the interface between a metal and an aqueous electrolyte solution, there is a mismatch in the type of charge carrier used. In the absence of a chemical mechanism to convert one type of charge into the other, the interface behaves as a capacitance: a change in the electronic charge density on the metal side is accompanied by a compensating change in ionic charge density on the solution side, so that electroneutrality is maintained.

The two types of charges can come very close to each other spatially without the possibility of neutralizing each other. This gives rise to an interfacial capacitance. [de Levie, Robert: The Admittance of the Interface between a Metal Electrode and an Aqueous Electrolyte Solution: Some Problems and Pitfalls, pp337–347 Annals of Biomedical Engineering, Special Issue]. Typically the interface between a metal and tissue is modeled as a resistor and a capacitor in parallel; at low currents the impedance associated with the capacitive leg of the circuit is small and the impedance associated with the resistive leg is large. Thus, any electrical discharge from electrically active tissue on the pulmonary vein side of the stent, or underlying the stent, will be hindered in its transmission to the atrium thereby limiting its ability to initiate an atrial fibrillation in the left atrium. Different biocompatible metals such as Platinum Iridium Alloys, ND35N, Titanium, nitinol, and Stainless Steels may be selected for different capacitive and resistive effects.

If pulmonary vein ablation is to be performed as the primary therapy and the stent is to be used to maintain pulmonary vein patency after ablation, then the necessary ablation catheter is passed through the catheter sheath into the left atrium to gain access to the pulmonary veins and perform the ablation prior to stent placement. The ablation catheter may be placed within the opening of the pulmonary veins or adjacent to the pulmonary veins to produce lesions using radiofrequency, ultrasound, microwave, laser, cryogenic or other energy transfer means as well as chemical means to kill the tissue locally. The damaged pulmonary vein or veins are now at risk for stenosis and stenting the pulmonary vein avoids the resulting pulmonary hypertension or occlusion. Stenting is performed by removing the ablation catheter of choice, and inserting a stenting catheter. The stenting catheter may use balloon expandable, self-expanding, or other types of expanding stents to maintain the patency of the pulmonary vein.

After one or more stents are placed in the pulmonary veins, with one or more catheters swapped out through the catheter sheath, the catheter sheath is removed, and the patient is closed. In most cases the opening through the fossa ovalis is very small and it heals up on its own. However, it is conceivable that a repair may be required in some patients using catheter techniques developed for closing septal defects.

The stent may be coated with a drug delivery compound or it may be partially made of a drug delivery compound. The stent is placed such that it delivers a sustained release of an antiarrhythmic drug which affects conduction locally. There are a number of viable pharmacologic therapies available. Drugs that predominantly affect slow pathway conduction include digitalis, calcium channel blockers, and beta-blockers. Drugs that predominantly prolong refractoriness, or time before a heart cell can be activated, produce conduction block in either the fast pathway or in accessory AV connections including the class IA antiarrhythmic agents (quinidine, procainimide, and disopyrimide) or class IC drugs (flecainide and propafenone). The class III antiarrhythmic agents (sotolol or amiodorone) prolong refractoriness and delay or block conduction over fast or slow pathways as well as in accessory AV connections. Temporary blockade of slow pathway conduction is usually achieved by intravenous administration of adenosine or verapamil. [Scheinman, Melvin: Supraventricular Tachycardia: Drug Therapy Versus Catheter Ablation, Clinical Cardiology Vol. 17, Supp. II-11-II-15 (1994)]. Other agents such as encainide, diltiazem, and nickel chloride are also available.

Figure 2:
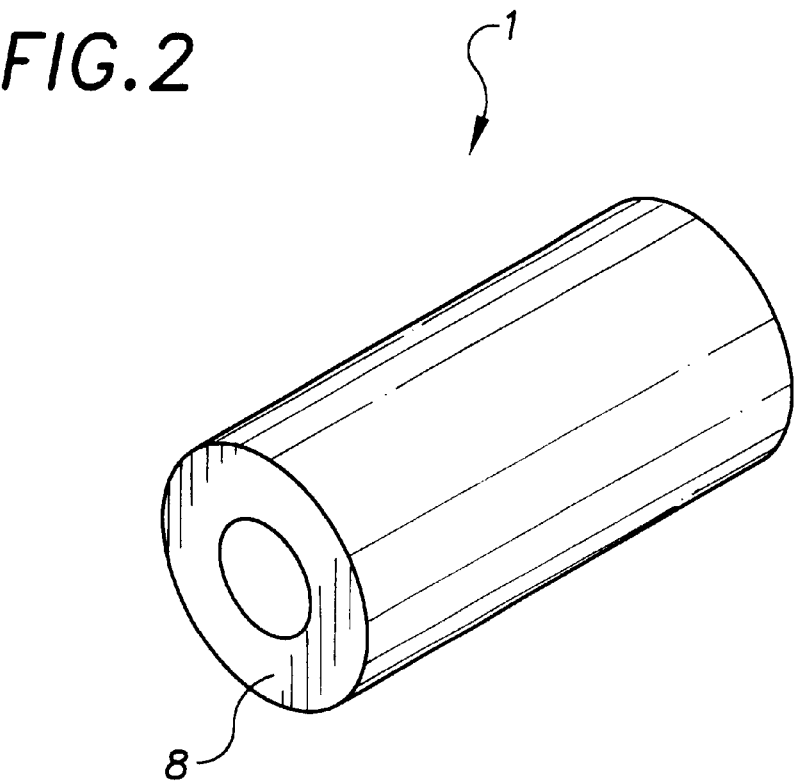
FIG. 2 is a schematic of a drug elution stent.
Figure 3:
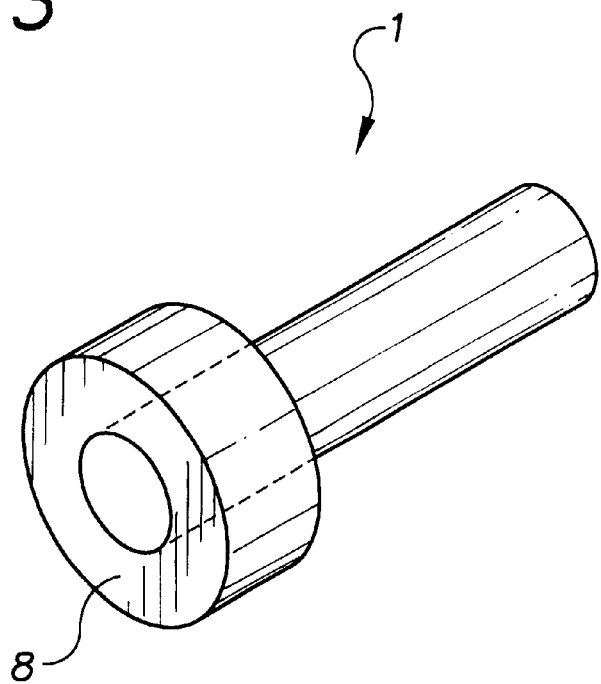
FIG. 3 is a schematic of a drug elution stent where only a narrow band of the stent is covered with a drug eluting compound.
Figure 4:
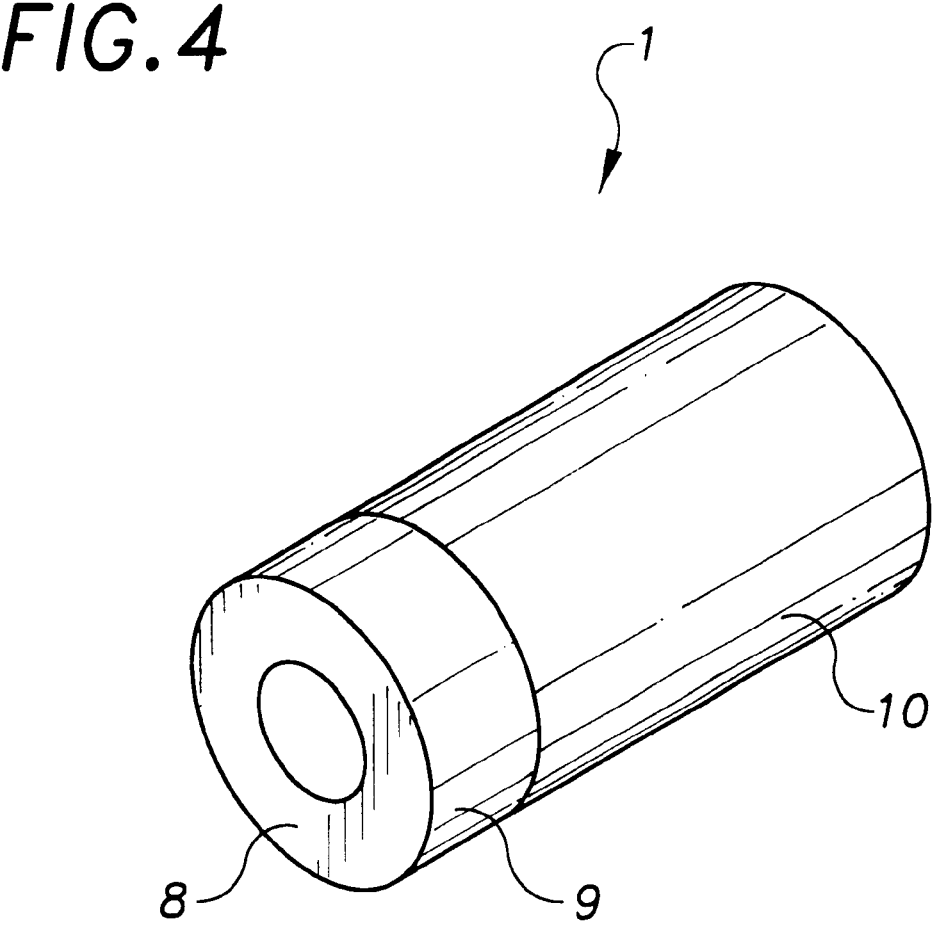
FIG. 4 is a schematic of a drug elution stent having a uniform coating of drug eluting compound and a coating covering a substantial portion of the stent such that the drug is eluted from a narrow band of the stent.
Figure 5:
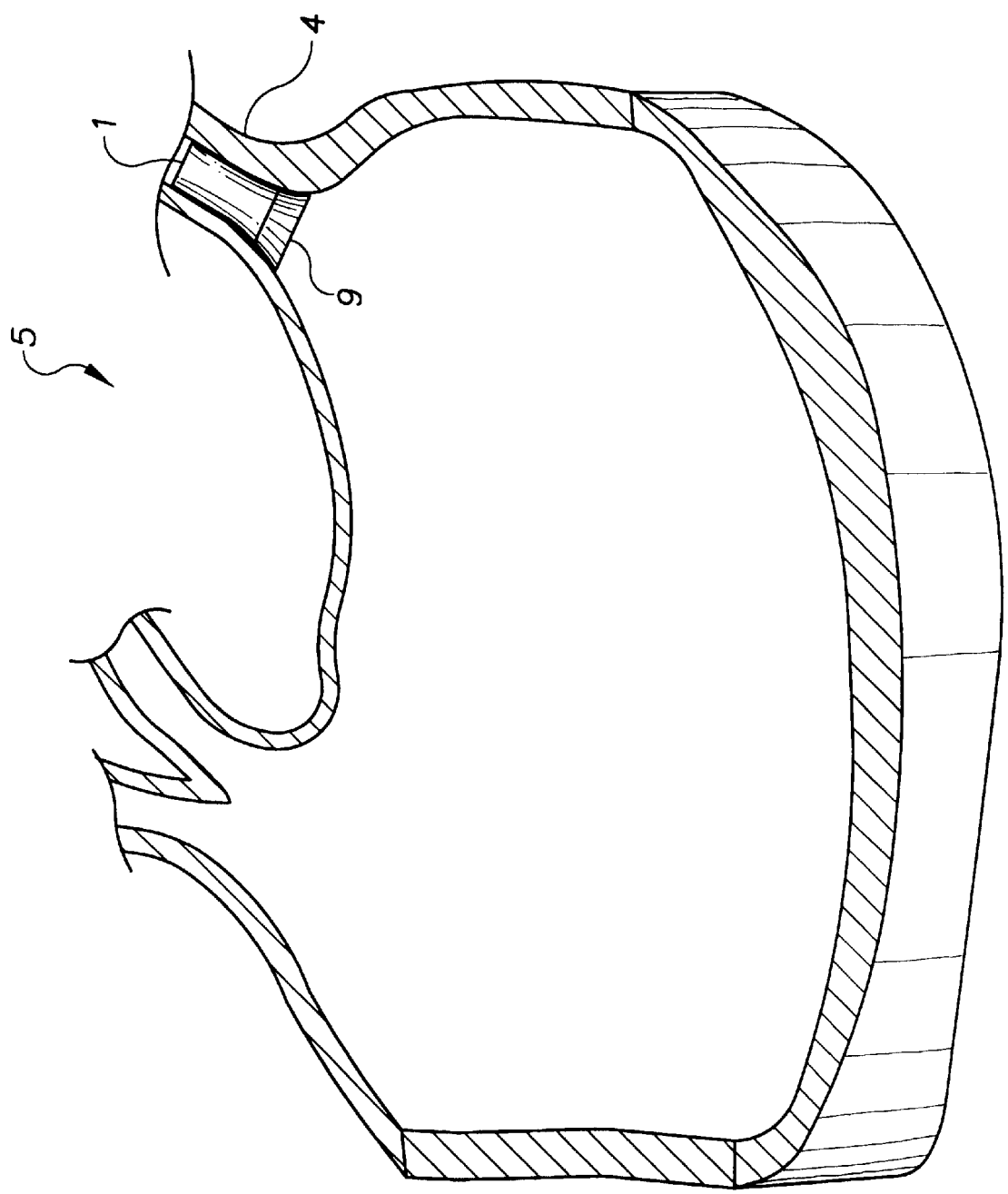
FIG. 5 is an isometric view of the left atrium having a stent deployed into the ostium of the target pulmonary vein, wherein the drug-eluting band is proximate the left atrium.

As in FIGS. 2, 3, and 4, the drugs may be placed on the stent 1 in a drug eluting coating 8. The drug eluting coating may be placed uniformly over the outer wall of the stent as in FIG. 2 or they may be placed in a narrow circumferential band on the proximal end of the stent as in FIG. 3. This band creates a short longitudinal segment of the stent which is capable of eluting drugs into the surrounding pulmonary vein. The remaining longitudinal segment of the stent is not covered with a drug-eluting compound. The stent is placed into the target pulmonary vein 4 such that the drug-eluting band is on the end of the stent nearest the left atrium after placement, as in FIG. 5.

As shown in FIG. 4, the drugs may be placed uniformly over or within the entire stent, while only a small band 9 is permitted to elute drugs outward into the pulmonary vein wall. This is accomplished by having a coating 10 covering a substantial longitudinal portion of the stent which prevents elution of the drug, thus leaving a small circumferential band which allows elution of the drug into the target pulmonary vein. The coating impedes the elution of drugs from the portion of the stent which is covers. This coating may be a thin layer of polyurethane or any other biocompatible coating impervious to the drug to be eluted. Having a small region 9 through which the drugs are eluted increases the ratio of drug volume to elution surface area. In other words, the large amount of drug-eluting compound can only be eluted through the small surface area, thus, increasing the ratio of drug volume to elution surface area. Where the stent is made of a polymer or hydrogel, the entire stent material may be loaded with the eluting drug.

The methods and devices described above can be accomplished with many embodiments of stents. Additionally, many stent materials and drug compounds may be substituted for the materials and drugs described. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

I claim:

1. A drug delivery stent comprising:
   a stent; and
   a drug-eluting coating on the stent, said drug eluting coating comprising a drug;
   the stent having a first longitudinal region through which the drug is eluted and a second longitudinal region through which the drug is not eluted;
   wherein the drug is an antiarrhythmic drug.

2. A drug delivery stent comprising:
   a stent;
   a drug-eluting compound uniformly covering the stent;
   a small first longitudinal region of the drug-eluting compound being capable of eluting a drug; and
   a cover disposed over a second longitudinal region of the drug eluting compound that prevents elution of a drug from the second longitudinal region;
   wherein the drug is an antiarrhythmic drug.

3. A drug delivery stent comprising:

a stent;

a drug incorporated into the stent; and a coating covering a substantial longitudinal portion of the stent, said coating inhibiting elution of the drug from the stent in said longitudinal portion, the drug being eluted from the portion of the stent not covered by the coating;

wherein the drug is an antiarrhythmic drug.

4. A drug delivery stent comprising:

a stent;

a drug-eluting compound, uniformly covering the stent, the drug-eluting compound comprising a drug; and a coating covering a first longitudinal portion of the drug-eluting compound, said coating impeding the elution of the drug from the stent, whereby the drug is eluted from the portion of the drug-eluting compound not covered by the coating;

wherein the drug is an antiarrhythmic drug.

5. A drug delivery stent comprising:

a stent having a first longitudinal region and a second longitudinal region;

a first coating disposed on the stent, said first coating capable of eluting a drug;

a second coating disposed on the stent and over the first coating, said second coating capable of inhibiting the drug from eluting;

wherein the second coating covers the first longitudinal region of the stent such that the drug may elute only from the second longitudinal region of the stent;

wherein the drug is an antiarrhythmic drug.

6. A drug delivery stent comprising:

a stent having a first longitudinal region and a second longitudinal region;

a first coating disposed on the stent on the first longitudinal region and the second longitudinal region, said first coating comprising a drug and a compound capable of eluting the drug;

a second coating disposed on the stent and over the first coating, said second coating being impermeable to the drug;

wherein the second coating is limited to the second longitudinal region of the stent such that the drug may elute only from the first longitudinal region of the stent;

wherein the drug is an antiarrhythmic drug.

* * * * *

UNITED STATES PATENT AND TRADEMARK OFFICE
CERTIFICATE OF CORRECTION

PATENT NO. : 6,716,242 B1  
DATED : April 6, 2004  
INVENTOR(S) : Altman

It is certified that error appears in the above-identified patent and that said Letters Patent is hereby corrected as shown below:

Column 5,
Line 23, the term "ND35N" should read -- MP35N --.

Signed and Sealed this

Third Day of August, 2004

JON W. DUDAS
*Acting Director of the United States Patent and Trademark Office*